United States Patent [19]
Ponticelli et al.

[11] Patent Number: 5,247,187
[45] Date of Patent: Sep. 21, 1993

[54] MEASURING INSTRUMENT AND MEASURING METHOD FOR IDENTIFYING PROPERTIES OF A SPECIMEN WITH MATCHED DUAL SOURCE CALIBRATION

[75] Inventors: Martin Ponticelli, Graz; Karl Simbuerger, Lebring, both of Austria

[73] Assignee: AVL Gesellschaft füer Verbrennungskraftmaschinen und Messtechnik mbH, Prof. Dr.Dr.h.c. Hans List, Austria

[21] Appl. No.: 946,608

[22] Filed: Sep. 18, 1992

[30] Foreign Application Priority Data

Sep. 20, 1991 [AT] Austria ............... 1898/91

[51] Int. Cl.$^5$ ............................. G01N 21/00
[52] U.S. Cl. ..................... 250/564; 250/214 R; 356/436
[58] Field of Search ............... 250/564, 565, 573, 574, 250/575, 214 R, 214 C; 356/434, 435, 436, 437, 438, 439

[56] References Cited

U.S. PATENT DOCUMENTS 4,640,621 2/1987 Rose ........................... 356/438
4,670,741 6/1987 Cole ........................... 250/573

Primary Examiner—David C. Nelms
Attorney, Agent, or Firm—Hill, Steadman & Simpson

[57] ABSTRACT

A measuring instrument and a method of measuring including providing an illumination arrangement having a plurality of independent illumination sources, a specimen region for conducting a specimen illuminated by the illumination arrangement, a measuring arrangement detecting radiation influenced by the specimen in the specimen region, the illumination arrangement having a plurality of independent aluminum sources which are energized by separate leads and separate switch elements that are operable to selectively operate either individually or in common for a linearity check.

11 Claims, 1 Drawing Sheet

MEASURING INSTRUMENT AND MEASURING METHOD FOR IDENTIFYING PROPERTIES OF A SPECIMEN WITH MATCHED DUAL SOURCE CALIBRATION

BACKGROUND OF THE INVENTION

The invention relates to improvements in measuring instruments and methods wherein an illumination arrangement emits electromagnetic radiation such as visible light into a specimen region. A measuring arrangement is positioned detecting the radiation influenced by the specimen with the radiation converted into a measured signal. More particularly, the invention relates to an improvement in such arrangement wherein a calibration means is provided for lowering the intensity of the radiation proceeding to the specimen during a linearity test of the instrument.

The invention is also directed to a measuring apparatus and method for identifying the properties of a specimen by documentation of the influenced electromagnetic radiation, particularly visible light by the specimen and whereby a controlled lowering of the intensity of the radiation proceeding to the specimen is undertaken for a linearity check.

Instruments and methods for measurements of specimens of the type above referred to are known in a variety of contexts and designs. For example, such known devices enable measurements of and statement outputs concerning the exhaust gas of internal combustion engines and this is often referred to as the opacimetric measuring method in exhaust gas measuring technology. Such measuring instruments and methods according to the opacimeter principle evaluate the attenuation of a radiation stream, particularly a light stream in the visible spectral range, generated by an illumination arrangement. This is detected by a suitable photo element or like arrangement with evaluation electronics on the basis of specimen gas presented in a specimen gas pipe. The attenuation or the extension of the light occurs due to various physical effects including absorption and dispersion.

Other devices and methods in this area of development also operate on the basis of reflection or incident light where the degree of blackening of filter paper is identified by measuring the reflectivity and is employed for output statements about the particle charging of exhaust gas or the like.

A halogen lamp having emission of light over a broad part of the visible spectral range is preferably currently utilized as an illumination source in cases which employ visible light. Other illumination sources, such as light emitting diodes having intensity maximums in the range of green light are also additionally employed.

In the evaluation of the measurement, in one method the measured signal level detected in the photo element of the measuring arrangement is proportional to the incident light stream, that is corresponding to the luminous intensity. This means that the measuring instrument basically works linearly.

In the practical realization, however, linearity errors in the measuring arrangement, particularly the saturation phenomena of the photo element, and errors in the evaluation electronics can be identified in addition to the shift to the zero point when the illumination arrangement is shut off. This is particularly due to dark currents, the entry of extraneous light, and offset errors of the evaluation electronics. This is in addition to a change in the sensitivity of the measuring arrangement, particularly triggered by aging of the illumination arrangement and of the photo element or the corresponding measuring arrangement, contamination of the beam path, and drift phenomena of the evaluation electronics.

In addition to containing the possibility of calibrating the zero point when the illumination arrangement is shut off, and of calibrating the maximum value with a clean specimen, standard embodiments of measuring instruments of the type described also contain a calibration means. Such calibration means is used in order to check the linearity of the measuring instrument in the individual measurement ranges with simple means, usually an individual measuring point in the middle of the measuring range.

The state of the art for the implementation of this simple linearity check is a filter disk with defined attenuation that can be inserted into the illumination path or in some instances, an insertable mechanical diaphragm with a defined aperture. This filter disk, or diaphragm, can be manually introduced or can be introduced with the assistance of an adjustment element such as a lifter magnet or an electric motor for automatic operation of the measuring instrument. In both instances, an optimally exactly defined part of the flowing illumination stream is occluded and the measured result identified by the measuring instrument as compared to the defined value.

In addition to the considerable mechanical outlay required for automated implementation, the disadvantage of linearity checks of a mechanism with diaphragms is that the geometric relationships enter into the measured result. For instance, the propagation of light through the specimen gas tube of an opacimeter, usually does not ensue in the form of parallel light rays. The outlay is therefore kept within justifiable limits. In particular, costly lenses or mirror systems are avoided. Changes in the light stream as particularly occur due to tolerances in the region of a lamp holder of the measurement head of the specimen gas pipe and of the diaphragm can, therefore, exhibit direct influence on the measured result given the linearity test with a mechanical diaphragm. The measurement error effected by said influences lies in the percentage range of known standard measuring instruments and method of the type referred to and thus lies one through several orders of magnitude above the typical linearity errors themselves.

Filter disks having defined attenuation of the illumination, that do not have the disadvantage of direct dependency on the geometrical arrangement, and that are therefore utilized for calibrations under laboratory conditions can only be utilized for an automated linearity check with considerable outlay. In particular, a falsification of the degree of attenuation due to the potential contamination under more difficult environment situations, as apply particularly to a factory measuring instrument, must be prevented.

It is accordingly an object of the present invention to provide an improved measuring instrument and method of the general type referred to such that the disadvantages of known instruments and methods do not occur such that exact and reliable linearity checks can be implemented.

A further object of the invention is to provide a measuring instrument so that simple and reliable means for linearity checks can be provided without expensive equipment construction.

A further object of the invention is to provide a measuring instrument of the type referred to wherein quick and reliable linearity checks can be conducted.

FEATURES OF THE INVENTION

In a measuring instrument of the type generally referred to, the objects are achieved in that the illumination arrangement includes a plurality of independent illumination sources. These illumination sources have separate energizing electrical leads with separate switch elements which can be selectively operated either individually or in common by the calibration means for a linearity check of the instrument. The corresponding embodiment of the measuring method of the invention is characterized in that the intensity contributions of a plurality of radiation sources to be selectively operated as individually defined are added and compared to the overall intensity of operation of all radiation sources.

The invention thus enables a linearity check with a plurality of light or illumination sources to be selectively switched, these being operated individually or in arbitrary groups as well as in chronological succession so that the pertinent photo currents can be obtained.

Still further, all illumination sources are activated in common and the aggregate photo current is identifiable. This aggregate configuration will also be subsequently utilized in the actual measurement. Light from a plurality of sources can be superimposed without interference and the arithmetic sum, given the assumption of a linear measuring arrangement, of the photo currents of the sources operated individually or in groups can be picked up by the measuring instrument and must correspond to the aggregate photo current given common operation of all light sources. This is also true for arbitrary individual combinations of a plurality of illumination sources. Potential, mutual occlusions, or different geometrical conditions of the individual illumination sources thereby have no negative effects since the conditions during individual operation do not change compared to mixed operation. The individual sources can also deliver different contributions to the aggregate photo current.

As in traditional arrangements having only one light source, the voltage source supplying the illumination arrangement can be advantageously executed in controlled fashion in order to keep the chronological drift of the measured values low and in order to also avoid a change in the supply of voltage due to the different load during a linearity check.

In addition to the above referred to higher precision of the linearity check, and the considerably reduced cost of the apparatus in an automatic linearity check, the apparatus and method of the invention obtains the advantage of enhanced reliability and useful life. This is obtained particularly with utilization of semiconductor switches or the like. In addition, an emergency operation of the instrument is also possible given a partial outage of the individual illumination sources. With the employment of incandescent lamps in the broadest sense as the illumination source, it is also conceivable that a need for maintenance can also be identified by comparing the individual partial streams of light.

In a preferred embodiment of the measuring instrument and in a preferred utilization of the method, the illumination arrangement includes two essentially identical illumination sources. These are arranged side by side or following one another thus enabling a simple design of the instrument with only a few additional parts and being adequate for most measuring purposes.

Other objects, advantages and features will become more apparent with the teaching of the principles of the invention in connection with the disclosure of the preferred embodiment thereof in the specification, claims and drawings, in which:

DESCRIPTION OF THE PREFERRED EMBODIMENT

Figure 1:
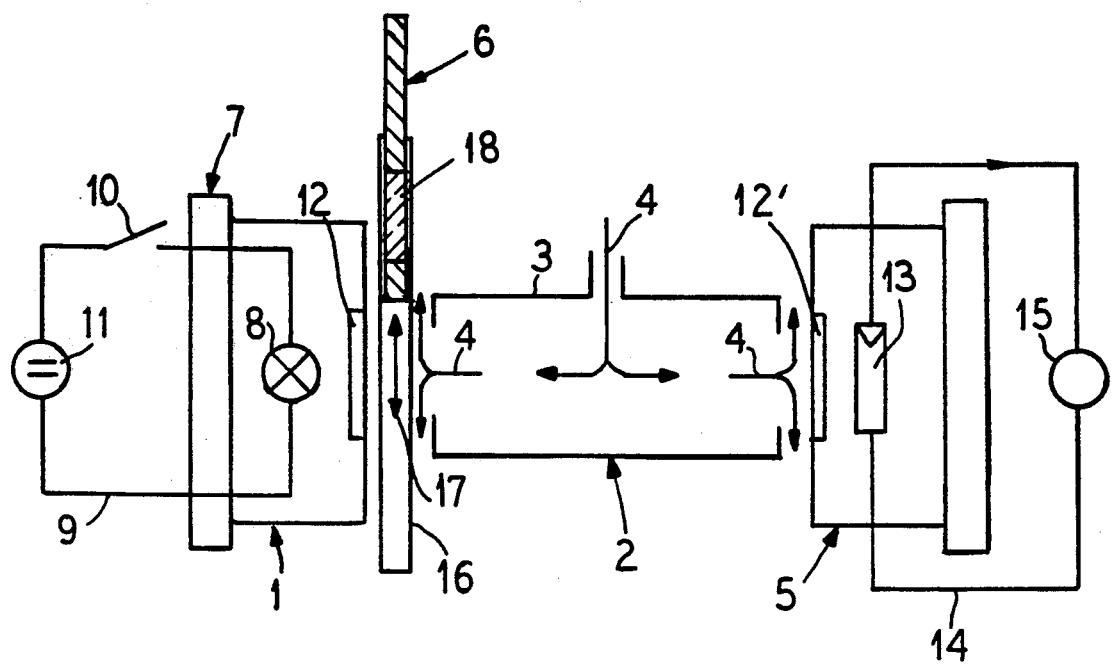
FIG. 1 illustrates schematically an opacimetric measuring instrument such as used by the prior art.

FIG. 1 illustrates a known structure wherein the measuring instrument includes an illumination arrangement 1 with a specimen region 2. In the specimen region, a gas pipe 3 is provided wherein the gaseous specimen flows as indicated by the arrow 4. The structure includes a measuring arrangement 5 and a calibration means 6. The illumination arrangement 1 includes a light head 7 which is comprised of a single illumination source 8 provided by way of example by a halogen lamp or the like. The lamp is connected electrically by a lead 9 to a switch 10 and to a voltage supply 11. At its exit side, the light head 7 is provided with a diffusing screen 12 for making the light stream uniform.

The measuring arrangement 5 lies diametrically opposite the light head relative to the specimen region 2 and is constructed somewhat similar to the light head. Filter disks 12' are arranged at the input side with a photo element 13 lying behind them. The photo element is connected via lines 14 to evaulation means 15 which may be an ammeter by way of example and in its simplest form.

A calibration means 6 is provided in the form of a filter disk 18 which is displaceable along a guide 16 as indicated by the double arrowed line 17. This is arranged between the exit diffusing screen 12 of the light head 7 and the specimen gas pipe 3. The filter disk 18 has a defined attenuation from which, when the filter disk 18 is inserted in front of the diffusing screen 12, occludes a precisely defined part of the light stream that otherwise flows through the specimen gas pipe 3 and wherewith the result identified overall with the measuring instrument can be compared to the defined rated value.

Figure 2:
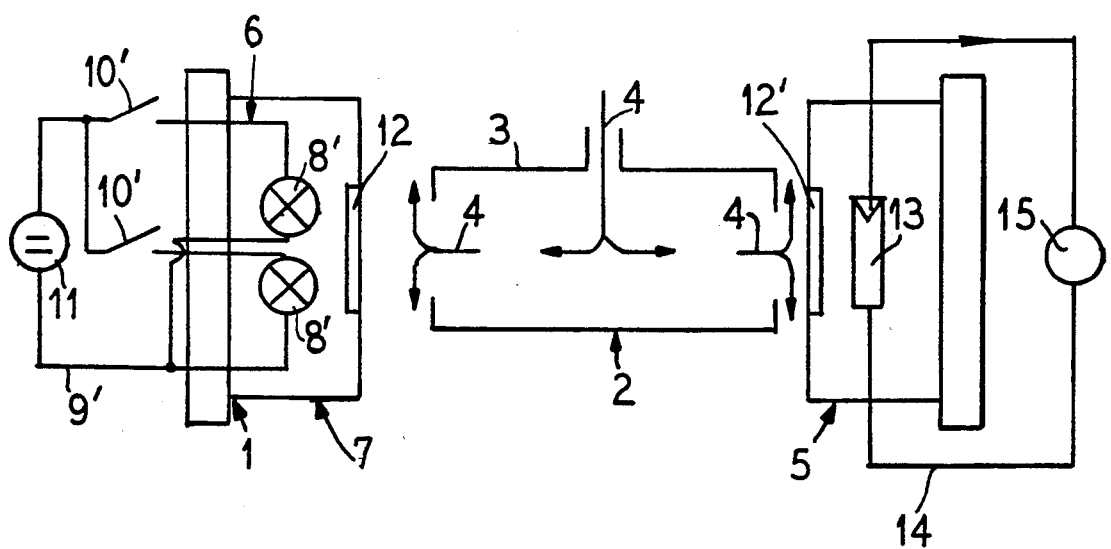
FIG. 2 is a schematic illustration of a measuring instrument embodying the features of the present invention.

In the illustration of the embodiment as shown in FIG. 2, the specimen region and the measuring arrangement 5 correspond generally to the measuring instrument shown in FIG. 1. Corresponding parts are numbered correspondingly, and the description of such parts in FIG. 1 also applies with respect to their functions and structure in FIG. 2.

The inventive features of FIG. 1 include the calibration means 6 and the corresponding altered illumination arrangement 1. This illumination arrangement now comprises a plurality of independent illumination sources shown as two illumination sources 8'. These illumination sources 8' are provided with separate electrical leads 9' and separate switch elements 10. These switch elements can be selectively operated individually or in common by the calibration means 6 for a linearity check of the instrument. The intensity contributions of the two illumination sources 8' can thus be individually identified with the measuring arrangement 5. The two illumination sources can be added in the evaluation means 15 and can be compared to the overall intensity with operation of both radiation sources 8'. This enables simple and precise linearity checks and also makes it possible to operate the overall apparatus with only one of the two illumination sources 8', if necesaary.

Apart from the specifically illustrated arrangement of the illumination structure 1 and the light head 7 in FIG. 2, a plurality of individual illumination sources 8' or a plurality of groups of illumination sources 7' can be provided. These also could have different mutual positions relative to each other since a mutual occlusion of the individual illumination soruces by one another produces no negative effects in the linearity check.

In operation, a specimen such as gas is directed into the region 3 as indicated by the arrowed lines 4. The illumination sources 8 and 8' are energized to direct light through the specimen via the diffusing screen 12. The light passes through the specimen and is modulated and received through the filter disks 12' by the photo element 13. The arrangement provides either an instantaneous or continuous measuring arrangement for identifying the properties of the specimen flowing along the arrowed lines 4.

In making the linearity check, the switches 10' are individually or conjunctively closed for the linearity check of the instrument as described above.

Thus, it will be seen there has been provided an improved measuring means which is of simplified construction and provides a simplified method as contrasted with what has heretofore been known.

We claim as our invention:

1. A measuring instrument for identifying properties of a specimen comprising in combination:
    an illumination source emitting electromagnetic radiation;
    means defining a specimen region positioned to be illuminated by said illumination source including a detection means for detecting radiation influenced by a specimen in the specimen region and converting a detection reading to a measured signal;
    and a calibration means for controllably lowering radiation emitted to the specimen in said specimen region during a linearity check;
    said illumination source including a plurality of independent sources having separate electrical leads with switch elements electively operable individually or in common by said calibration means for said linearity check.

2. A measuring instrument for identifying properties of a specimen constructed in accordance with claim 1:
    wherein said plurality of independent illumination sources comprise two essentially identical illumination sources.

3. A measuring instrument for identifying properties of a specimen constructed in accordance with claim 2:
    wherein said illumination sources are arranged side by side.

4. A measuring instrument for identifying properties of a specimen constructed in accordance with claim 1:
    wherein said specimen region is constructed to conduct a gaseous specimen.

5. A measuring instrument for identifying properties of a specimen constructed in accordance with claim 1:
    wherein said detection means includes filter disks and a photo element establishing a measuring arrangement.

6. A measuring instrument for identifying properties of a specimen constructed in accordance with claim 1:
    wherein said illumination source is positioned at one side of said specimen region and said detection means is positioned diametrically opposite the location of the illumination source relative to the specimen region so that said illumination passes through the specimen region to the detection means.

7. A method for measuring and identifying properties of a specimen comprising the steps:
    applying an illumination source emitting electromagnetic radiation including a plurality of sources to a specimen region to document the influence of the radiation by the specimen;
    controllably lowering the intensity of the radiation emitted to the specimen for a linearity check;
    and individually identifying the intensity contributions of the plurality of radiation sources and comparing to the overall intensity of the added sources.

8. A method for measuring and identifying properties of a specimen in accordance with the steps of claim 7:
    wherein the illumination source comprises two individual radiation sources.

9. A method of measuring and identifying properties of a specimen comprising the steps:
    providing an illumination source for emitting electromagnetic radiation in the form of a plurality of illumination sources;
    providing a specimen region positioned to be illuminated by said illumination source and including a detection means for detection of radiation influenced by the specimen in the specimen region and converting the detection reading to a measured signal;
    calibrating the illumination source by controllably lowering the radiation emitted to the specimen in the specimen region and conducting a linearity check;
    and selectively switching to the individual illumination sources and switching to said sources in common for calibrating for the linearity check.

10. A method of measuring and identifying properties of a specimen in accordance with the steps of claim 9:
    wherein two identical illumination sources are provided.

11. A method of measuring and identifying properties of a specimen in accordance with the steps of claim 9:
    wherein a detection means is provided diametrically opposite the illumination source for detecting the radiation influenced by the specimen.

* * * * *